United States Patent [19]
Kato

[11] Patent Number: 5,490,508
[45] Date of Patent: Feb. 13, 1996

[54] MAGNETIC RESONANCE IMAGING DIAGNOSIS APPARATUS HAVING MAT FOR USE WITH SMALL BODY

[75] Inventor: Yutaka Kato, Tochigiken, Japan

[73] Assignee: Kabushiki Kaisha Toshiba, Kanagawa, Japan

[21] Appl. No.: 198,234

[22] Filed: Feb. 16, 1994

[30] Foreign Application Priority Data

Feb. 19, 1993 [JP] Japan .................................. 5-030544

[51] Int. Cl.⁶ .................................................. A61B 5/055
[52] U.S. Cl. ...................................... 128/653.5; 324/318
[58] Field of Search .......................... 128/653.2, 653.5; 324/309, 318, 322; 5/601

[56] References Cited

U.S. PATENT DOCUMENTS

| | | | |
|---|---|---|---|
| 4,684,894 | 8/1987 | Bliehall | 128/653.5 |
| 4,791,371 | 12/1988 | Krol | 128/653.5 |
| 5,197,474 | 3/1993 | Englund et al. | 128/653.5 |

FOREIGN PATENT DOCUMENTS

| | | | |
|---|---|---|---|
| 4295337 | 10/1992 | Japan | 128/653.5 |
| 4279149 | 10/1992 | Japan | 128/653.2 |
| 5123310 | 5/1993 | Japan | 128/653.5 |

*Primary Examiner*—Ruth S. Smith
*Attorney, Agent, or Firm*—Ronald L. Yin; Limbach & Limbach

[57] ABSTRACT

A magnetic resonance diagnosis apparatus having a diagnosis mat by which the position of the surface coil is accurately confirmed. The magnetic resonance imaging diagnosis apparatus includes a gantry for enclosing a biological body so as to provide an imaging area; a mat portion having a slot therein in a lateral side thereof wherein the mat portion is provided above a tabletop that is movable into and out of the gantry; and surface coil for applying electromagnetic waves to the biological body, and which is slidably inserted to the slot of the mat portion so that a position of the coil means is accurately indexed and observed.

4 Claims, 4 Drawing Sheets

MAGNETIC RESONANCE IMAGING DIAGNOSIS APPARATUS HAVING MAT FOR USE WITH SMALL BODY

BACKGROUND OF THE INVENTION

1. Technical Field

The present invention relates to a diagnosis mat and a infant-use mat under magnetic resonance imaging (MRI) which supports a biological body to be examined by an MRI diagnostic apparatus.

2. Background Art

In recent years of active development for medical diagnosis apparatus, there has been often utilized a magnetic resonance (MR) diagnosis apparatus in which a biological body under medical examination is imaged without being operated on or being cut out. In the magnetic resonance diagnosis apparatus, the biological body is placed on a tabletop and is transported into a gantry so that the biological body is photographed in a photographing region of the gantry. Therefore, the body to be examined must be at a standstill position.

While the requirement for the body to be at a stationary position is not difficult to be achieved for grown-up people, however, it often creates difficulties among infants or small children. Thus, there is now used a mat to support a patient such as the infant and small child.

FIG. 7 shows such a mat to be used for the MR apparatus. In FIG. 7, a plurality of belts 3 (four belts) are attached to a side of the mat and there are provided four buckles 2, on other side, to fasten respective belts 3.

Referring still to FIG. 7, the patient placed on the mat 1 is firmly supported by the belts 3 and the buckles 2. In order that a nuclear magnetic resonance (NMR) signal is received from a desired position of the patient, part of the mat 1 is a hollow and a short side of the mat 1 has an opening so that a surface coil 5 can be inserted inside of the mat 1. The surface coil 5 is fixed to a tray 4 and can be pulled out by a pullout rod 6. In other words, the position of the surface coil 5 can be adjusted by pulling and inserting the pullout rod 6.

However, in the magnetic resonance apparatus as shown in FIG. 7, the surface coil 5 is inserted into a longitudinal direction of the mat 1. Therefore, the position of the surface coil 5 can not be visually confirmed, so that the position of the surface coil 5 is determined based on length of the pullout rod 6 inserted. Therefore, there is a drawback where the position of the surface coil 5 can not be accurately set without providing a scale.

Moreover, when a patient such as infant or small child is examined and imaged, an anesthetic is sometimes required to avoid undesired movement by the patient. Moreover, a few piles of towels need be placed under the patient in order to adjust the height to obtain an appropriate imaging region thus taking much time.

Accordingly, since the surface coil 5 is inserted from the longitudinal direction of the mat 1, the position of the surface coil 5 can not be accurately confirmed. Moreover, when the infant or small child is imaged by the MR apparatus, the patient goes through physical pain by taking an anesthetic or the like and many efforts are required to properly adjust the height and position of the patient.

SUMMARY OF THE INVENTION

In view of the foregoing drawbacks, it is therefore an object of the present invention to provide a magnetic resonance diagnosis apparatus having a diagnosis mat by which the position of the surface coil is accurately confirmed.

Another object of the present invention is to provide a small-body-use mat for magnetic resonance apparatus to facilitate imaging of the small biological body to be examined.

According to one aspect of the present invention, there is provided a magnetic resonance imaging diagnosis apparatus in which a biological body to be examined is placed over a tabletop thereon, in which the apparatus comprises: a gantry for providing an imaging area; a mat portion having a slot therein in a lateral side thereof, the mat portion being provided above the tabletop that is movable into and out of the gantry; and radio frequency coil means for applying electromagnetic waves to the biological body, and which is slidably inserted to the slot of the mat portion so that a position of the coil means is accurately observed and aligned.

According to another aspect of the present invention there is provided an magnetic resonance imaging diagnosis apparatus, including: a mat portion for use with a small biological body to be medically examined wherein the mat is equipped with a belt, attached thereto, for securely supporting the small biological body; and handle means, attached to the mat portion, for facilitating movement along a tabletop.

BRIEF DESCRIPTION OF THE DRAWINGS

These and other objects, features and advantages of the present invention will become more apparent from the following description of the preferred embodiment taken in conjunction with the accompanying drawings, in which.

DETAILED DESCRIPTION OF THE PREFERRED EMBODIMENTS

Features of the present invention will become apparent in the course of the following description of exemplary embodiments which are given for illustration of the invention and are not intended to be limiting thereof. Embodiments of the present invention will now be described with reference to the drawings.

Figure 1:
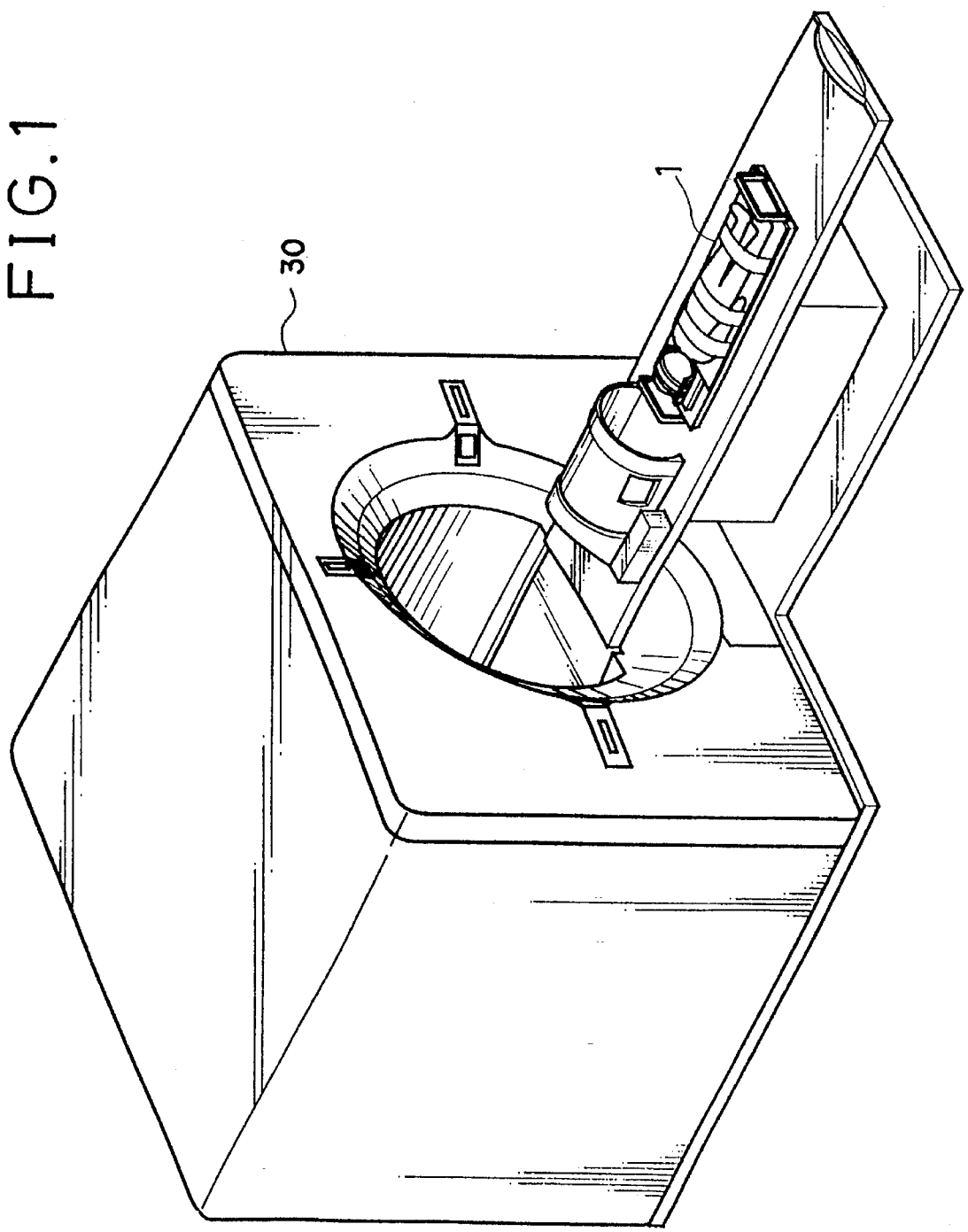
FIG. 1 is a perspective view showing an overall configuration for a magnetic resonance imaging diagnosis apparatus according to the present invention.

FIG. 1 is a perspective view showing an overall configuration for a magnetic resonance imaging (MRI) diagnosis apparatus according to the present invention, including a gantry 30 and a mat 1.

Figure 2:
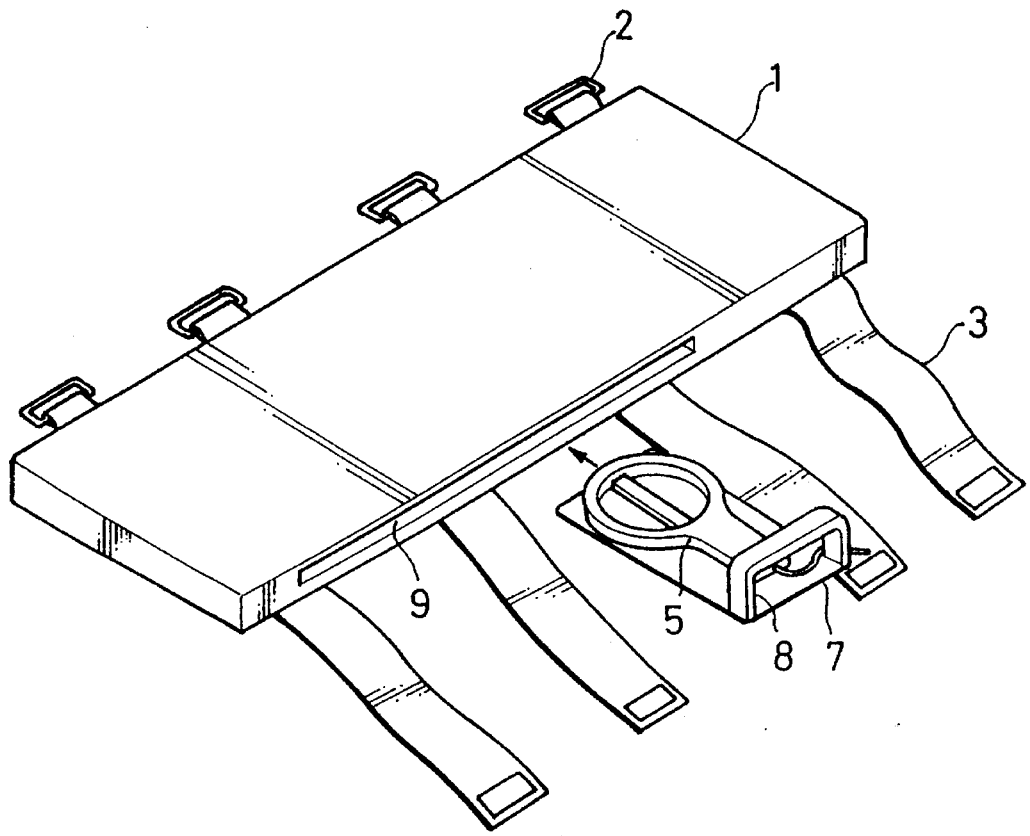
FIG. 2 is a perspective view showing a mat according to the first embodiment of the present invention.

FIG. 2 is a perspective view showing a mat according to the first embodiment of the present invention.

Referring to FIG. 2, the mat for use with the MRI diagnosis apparatus includes a mat 1, a belt 3 (four belts in this example shown in FIG. 2) attached to a lateral side of the mat 1, and a buckle 2 provided (four buckles in this example shown in FIG. 2) at other side of the mat 1 corresponding to the belt 3. There is provided an opening portion in the lateral side of the mat 1, so that part of inside of the mat 1 has a hollow portion.

Referring still to FIG. 2, the mat 1 further includes a tray 7 which can be inserted into and pulled out of the hollow portion 9. A surface coil 5 is attached to the tray 7. The surface coil 5 applies electromagnetic waves to the biological body, and it receives nuclear magnetic resonance (NMR) signals from the biological body as well. The tray 7 is also equipped with a handle 8 so that an operator thereof can easily operate the tray 7 by holding the handle 8. The operator inserts the tray 7 into the opening portion 9 and moves the tray 7 in either right or left direction so that the surface coil 5 can be placed at a desired position.

Figure 3:
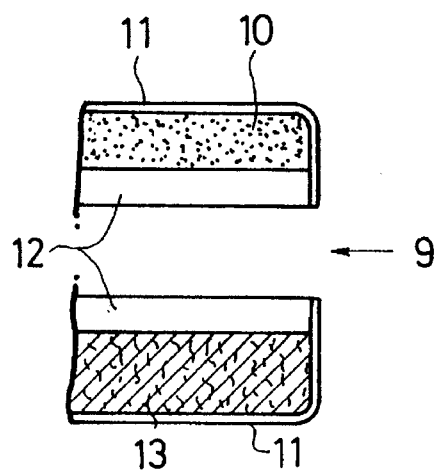
FIG. 3 is a cross sectional view of the opening portion 9 shown in FIG. 2.

FIG. 3 is a cross sectional view of the opening portion 9 shown in FIG. 2.

Referring to FIG. 3, an upper layer of the mat presents a two-layer construction comprised of cushion material 10 and core material 12 such as ABS material, and the surface of the upper layer is covered with cover material 11. A lower layer of the mat also has a two-layer construction comprised of the core material 12 and a spacer 13, and the surface of the lower layer is covered with the cover material 11. The spacer 13, such as polyethylene foam, serves to provide a sufficient height for the mat 1. Strength of the opening portion 9 is guaranteed by the core material 12.

Accordingly, in the mat there is provided the opening portion extending from the lateral side of the mat, so that the operator can confirm accurately the position of the tray to which the surface coil is attached. This configuration employed by the first embodiment makes alignment of the surface coil to the biological body significantly easy and accurate.

Figure 4:
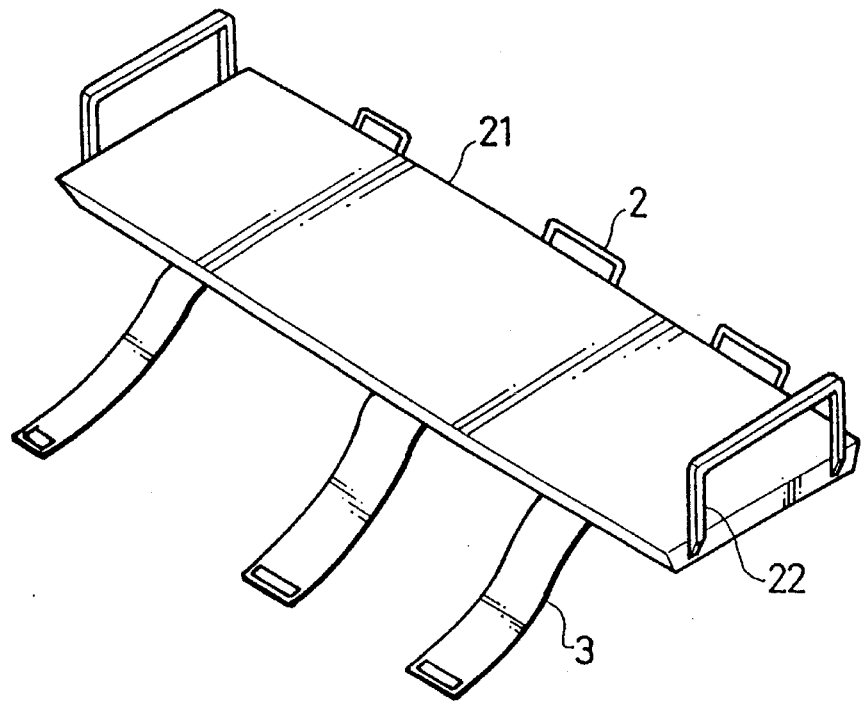
FIG. 4 is a mat prepared for an infant or small child for use with MRI diagnosis apparatus, according to the second embodiment of the present invention.

FIG. 4 is a mat prepared for an infant or small child for use with MRI diagnosis apparatus, according to the second embodiment of the present invention.

Referring to FIG. 4, small-child mat 21 has an appropriate size to place the small child body thereon. The small-child mat 21 has a belt 3 in a lateral side of the mat and a buckle 2 in other side. In a short side of the mat 21, there is attached a handle 22 so that the operator can hold the handle in order to move the mat easily.

Figure 5:
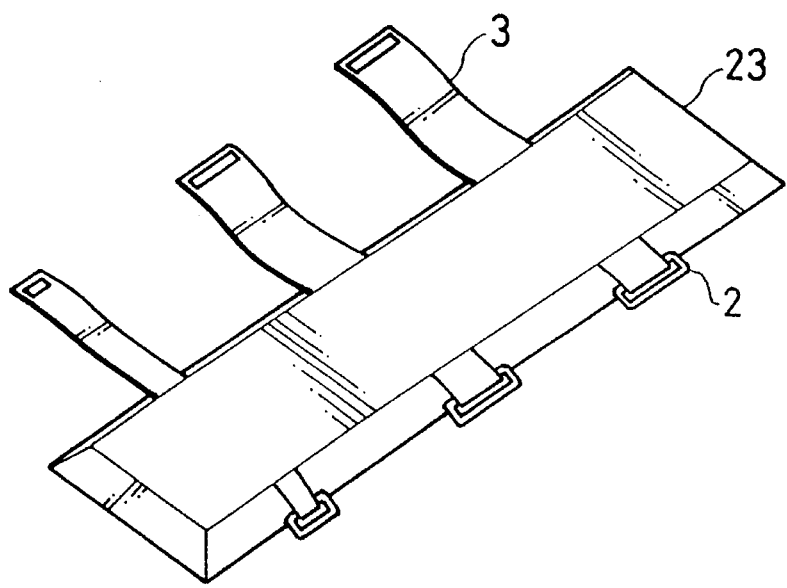
FIG. 5 is a perspective view showing the reverse side of small-child mat 21 in which there is provided a solid plate 23 which is smoothly slidable along the tabletop.

With reference to FIG. 5, which illustrates the reverse side of the small-child mat 21, there is provided a solid plate 23 which is smoothly slidable along the tabletop. On top of the solid plate 23, there may be provided a mat sponge or the like. Thus, the solid plate 23 can move smoothly on the tabletop.

By employing the small-child mat for use with MRI diagnosis apparatus, the small child body to be examined can be firmly supported without pain and the small-child mat can be smoothly slided so that the small child body can be set to an appropriate imaging position.

Figure 6A:
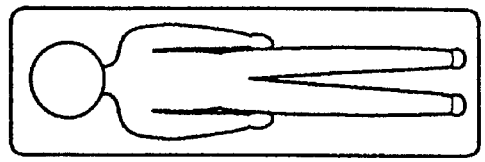
FIG. 6A is a top view of the mat for use with the infant patient of, for example, less than three years of age.
Figure 6B:
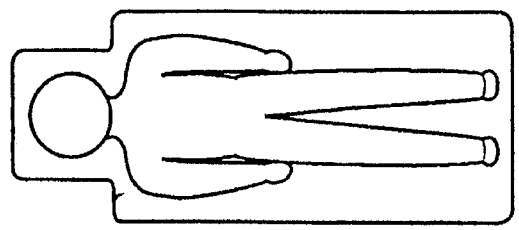
FIG. 6B is a top view of the mat for use with the small child of, for example, three to seven years old of age.
Figure 7:
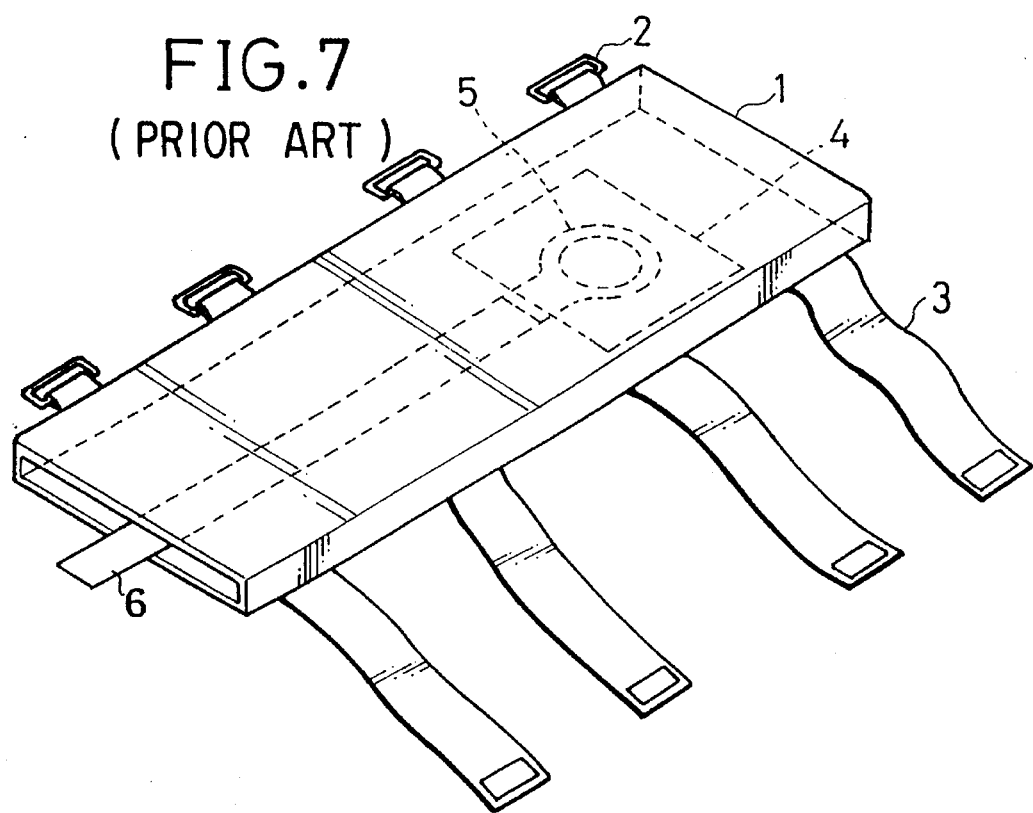
FIG. 7 shows a mat to be used for the MR apparatus.

Moreover, different configurations for the small-child mat 21 may be provided separately based on the body size of the small-child. Referring to FIG. 6A, for example, an infant patient of less than three years old of age is placed on the mat having the same width from head to leg portions. On the other hand, referring to FIG. 6B, the shape of the mat for use with small child of, for example, three year old through seven year old may be such that the width for the head portion is narrowed down. Thereby, when the infant is photographed, the whole body can be photographed using a head coil that is used for photographing adults.

In summary, according to the first embodiment of the present invention, there is provided the opening portion extending from the lateral side of the mat for use with MRI diagnosis apparatus, and the surface coil is inserted to the opening portion. Thereby, the operator can set easily and accurately the position of the surface coil while confirming that with his own eyes. Therefore, efficiency for carrying out MR diagnosis is significantly improved.

According to the second embodiment of the present invention, the small child patient can be firmly supported without pain to the patient so as to be easily moved into the imaging region. Thereby, the MR imaging for the small child can be easily carried out.

Besides those already mentioned above, many modifications and variations of the above embodiments may be made without departing from the novel and advantageous features of the present invention. Accordingly, all such modifications and variations are intended to be included within the scope of the appended claims.

What is claimed is:

1. In a magnetic resonance imaging diagnosis apparatus having means for generating magnetic and gradient fields in a space and radio frequency coil means for receiving nuclear magnetic resonance signals from said space, and means for providing an image using the nuclear magnetic resonance signals received from the radio frequency coil means, wherein the improvement comprises:

a gantry for enclosing the space;

a tabletop which is slidably insertable into said space enclosed by said gantry;

a mat having a length dimension and a width dimension with the length dimension greater than the width dimension and a slot therein in the length dimension, the mat being provided above the tabletop; and wherein the radio frequency coil means is slidably inserted in the slot of the mat so that a position of the coil means relative to the mat in a direction substantially parallel to the length dimension of the mat can be accurately observed and aligned.

2. The apparatus of claim 1, wherein the radio frequency coil means includes handle means for facilitating movement of the radio frequency coil means through the slot.

3. The apparatus of claim 1, wherein the radio frequency coil means includes a surface coil.

4. The apparatus of claim 1, wherein the mat further comprises:

an upper layer comprising cushion material and core material; and a lower layer comprising the core material and a spacer, wherein the slot is interposed between the upper layer and the lower layer.

\* \* \* \* \*